United States Patent
Finn et al.

(10) Patent No.: US 11,428,797 B2
(45) Date of Patent: Aug. 30, 2022

(54) RADAR DETECTION SYSTEM

(71) Applicant: Carrier Corporation, Palm Beach Gardens, FL (US)

(72) Inventors: Alan Matthew Finn, Hebron, CT (US); Nicholas Charles Soldner, Mountainview, CA (US); Joseph Zacchio, Wethersfield, CT (US); Ziyou Xiong, Wethersfield, CT (US); Cagatay Tokgoz, Beaumont, TX (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 672 days.

(21) Appl. No.: 16/475,893

(22) PCT Filed: Jan. 5, 2018

(86) PCT No.: PCT/US2018/012556
§ 371 (c)(1),
(2) Date: Jul. 3, 2019

(87) PCT Pub. No.: WO2018/129294
PCT Pub. Date: Jul. 12, 2018

(65) Prior Publication Data
US 2019/0346550 A1 Nov. 14, 2019

Related U.S. Application Data
(60) Provisional application No. 62/443,354, filed on Jan. 6, 2017.

(51) Int. Cl.
*G01S 13/56* (2006.01)
*A61B 5/0205* (2006.01)
(Continued)

(52) U.S. Cl.
CPC ............ *G01S 13/56* (2013.01); *A61B 5/0205* (2013.01); *A61B 5/0507* (2013.01); *G01S 13/86* (2013.01); *A61B 5/024* (2013.01); *A61B 5/0816* (2013.01)

(58) Field of Classification Search
CPC . G01S 13/56; G01S 13/86; G01S 7/40; A61B 5/0205; A61B 5/0507; A61B 5/024; A61B 5/0816; A61B 5/6889
See application file for complete search history.

(56) References Cited

U.S. PATENT DOCUMENTS

| | | | |
|---|---|---|---|
| 4,435,699 A | 3/1984 | Tacussel | |
| 6,816,073 B2 | 11/2004 | Vaccaro et al. | |

(Continued)

FOREIGN PATENT DOCUMENTS

| | | |
|---|---|---|
| WO | 2015174879 A1 | 11/2015 |
| WO | 2016038148 A1 | 3/2016 |

OTHER PUBLICATIONS

Adib, F. et al. "Smart Homes that Monitor Breathing and Heart Rate"; Massachusetts Institute of Technology, 32 Vassar Street, Cambridge, MA 02139; Apr. 18-23, 2015; Retrieved from http://dx.doi.org/10.1145/2702123.2702200; 9 Pages.

(Continued)

*Primary Examiner* — Omeed Alizada
(74) *Attorney, Agent, or Firm* — Cantor Colburn LLP

(57) ABSTRACT

A radar presence detection system is configured to detect oscillations within a building. The radar presence detection system includes an accelerometer, a radar, and a processing unit. The accelerometer is attached to the building and configured to detect structural vibration waves. The radar is configured to transmit a monitoring wave and receive a reflected wave. The processing unit includes a filter, an adaptive filter, and a detector. The filter is configured to receive a first signal indicative of the reflected wave and (Continued)

output a filtered reflected wave signal spanning a frequency range indicative of an oscillation within the building. The adaptive filter is configured to receive a second signal indicative of the structural vibration wave signal and output a focused vibration signal spanning a frequency range for the cancellation of vibration noise.

16 Claims, 4 Drawing Sheets

(51) Int. Cl.
    *A61B 5/0507*     (2021.01)
    *G01S 13/86*     (2006.01)
    *A61B 5/024*     (2006.01)
    *A61B 5/08*     (2006.01)

(56) References Cited

U.S. PATENT DOCUMENTS

| | | | |
|---|---|---|---|
| 7,507,203 B2 | 3/2009 | Sebastian et al. | |
| 7,567,200 B1 | 7/2009 | Osterweil | |
| 7,679,545 B2 | 3/2010 | Rausch et al. | |
| 7,811,234 B2 | 10/2010 | McGrath | |
| 7,894,305 B2 | 2/2011 | Sabatier et al. | |
| 8,068,051 B1 | 11/2011 | Osterweil | |
| 8,264,396 B2 | 9/2012 | Peczalski et al. | |
| 8,454,528 B2 | 6/2013 | Yuen et al. | |
| 8,461,989 B2 | 6/2013 | Romero et al. | |
| 8,597,196 B2 | 12/2013 | Kishi et al. | |
| 8,686,362 B2 | 4/2014 | Bakhtiari et al. | |
| 9,000,973 B2 | 4/2015 | Hyde et al. | |
| 9,035,775 B2 | 5/2015 | Margon | |
| 2006/0061504 A1 | 3/2006 | Leach, Jr. et al. | |
| 2008/0211668 A1 | 9/2008 | Dixon et al. | |
| 2009/0058711 A1* | 3/2009 | Dixon | G01S 13/56 342/28 |
| 2010/0026550 A1 | 2/2010 | Rosenbury | |
| 2010/0027737 A1 | 2/2010 | Mostov | |
| 2010/0141443 A1* | 6/2010 | Romero | G08B 29/20 340/552 |
| 2010/0152600 A1 | 6/2010 | Droitcour et al. | |
| 2011/0025545 A1* | 2/2011 | Cook | G01S 13/5242 342/22 |
| 2013/0002434 A1 | 1/2013 | Cuddihy et al. | |
| 2013/0113647 A1 | 5/2013 | Sentelle et al. | |
| 2013/0241764 A1 | 9/2013 | Kozma et al. | |
| 2015/0241555 A1 | 8/2015 | Lin et al. | |
| 2015/0260835 A1 | 9/2015 | Widmer et al. | |
| 2017/0282828 A1* | 10/2017 | Carenza | B60R 21/01512 |

OTHER PUBLICATIONS

Huang, M. et al. "A Self-Calibrating Radar Sensor System for Measuring Vital Signs"; IEEE Transactions on Biomedical Circuits and Systems, vol. 10, No. 2, Apr. 2016; Retrieved from http://www.ieee.org/publications_standards/publications/rights/index.html; 11 Pages.

ISR for App. No. PCT/US2018/012556 dated Apr. 26, 2018; 5 pages.

WO for App. No. PCT/US2018/012556 dated Apr. 26, 2018; 10 pages.

* cited by examiner

RADAR DETECTION SYSTEM

CROSS-REFERENCE TO RELATED APPLICATIONS

This application claims the benefit of PCT/US2018/012556 filed Jan. 5, 2018, which claims priority to U.S. Provisional Application No. 62/443,354 filed Jan. 6, 2017, which is incorporated herein by reference in its entirety.

BACKGROUND

The present disclosure relates to a detection system, and more particularly to a radar presence detection system.

Utilization of relatively inexpensive radar to detect human presence through motion, heartbeat and/or respiration is an emerging technology. The same technology may also be used to monitor the heartbeat, respiration, or vital signs of any species of animal. Yet further, the technology may be used to detect unusual vibration of, for example, equipment. The radar is typically attached to a building wall or ceiling. Unfortunately, building vibration may contribute toward electronic noise that degrades the detection capability of vital signs or vibration, indicative of, for example, a human presence. Various means of isolating such noise from the radar is desirable.

BRIEF DESCRIPTION

A radar presence detection system configured to detect oscillations within a building according to one, non-limiting, embodiment of the present disclosure includes an accelerometer attached to the building and configured to detect structural vibration waves; a radar configured to transmit a monitoring wave and receive a reflected wave; a processing unit configured to receive a reflected wave signal from the radar indicative of the reflected wave, and a vibration wave signal indicative of the structural vibration wave, the processing unit including a filter, an adaptive filter and a detector, wherein the filter is configured to receive a first signal indicative of the reflected wave signal and output a filtered reflected wave signal spanning a frequency range indicative of an oscillation within the building, and the adaptive filter being configured to receive a second signal indicative of the structural vibration wave signal and output a focused vibration signal spanning the frequency range for the cancellation of vibration noise, and wherein the detector is configured to receive a third signal indicative of at least the filtered reflected wave signal and output an oscillation signal indicative of at least the detection of the oscillation.

Additionally to the foregoing embodiment, the processing unit is a vital sign processing unit, the filtered reflected wave signal is a vital sign reflected wave signal, and the oscillation is a vital sign; and, wherein the vital sign processing unit includes a summation module configured to receive the vital sign reflected wave signal and the focused vibration signal, subtract the focused vibration signal from the vital sign reflected wave signal, and output a corrected vital sign signal received by the detector.

In the alternative or additional thereto, in the foregoing embodiment, the adaptive filter is a long adaptive filter.

In the alternative or additional thereto, in the foregoing embodiment, the processing unit is a vital sign processing unit and the oscillation is a vital sign, and the vital sign processing unit includes a first analog-to-digital converter configured to receive the reflected wave signal and output a digitized reflected wave signal as the first signal.

In the alternative or additional thereto, in the foregoing embodiment, the vital sign processing unit includes a second analog-to-digital converter configured to receive the vibration wave signal and output a digitized vibration signal as the second signal.

In the alternative or additional thereto, in the foregoing embodiment, the filtered reflected wave signal is a vital sign reflected wave signal, and wherein the vital sign processing unit includes a summation module configured to receive the vital sign reflected wave signal and the focused vibration signal, subtract the focused vibration signal from the vital sign reflected wave signal, and output a corrected vital sign signal received by the detector.

In the alternative or additional thereto, in the foregoing embodiment, the adaptive filter is configured to cancel a broad band of vibration frequencies within the frequency range.

In the alternative or additional thereto, in the foregoing embodiment, the adaptive filter includes a plurality of taps with a sufficient number of taps so that a full wave at a minimum respiration frequency is accommodated.

In the alternative or additional thereto, in the foregoing embodiment, the oscillation is at least one vital sign that includes at least one of a respiration rate and a heartbeat.

In the alternative or additional thereto, in the foregoing embodiment, the radar is remotely located from the accelerometer.

In the alternative or additional thereto, in the foregoing embodiment, the radar presence detection system includes an actuator attached to the building and the accelerometer, wherein the actuator receives and is driven by the focused vibration signal to cancel vibration noise.

In the alternative or additional thereto, in the foregoing embodiment, the adaptive filter is at least one of a LMS filter, a NLMS filter, a RLS filter, and a DMI filter.

In the alternative or additional thereto, in the foregoing embodiment, the accelerometer is not located at any vibration node of the building.

In the alternative or additional thereto, in the foregoing embodiment, the accelerometer is co-located with the radar.

In the alternative or additional thereto, in the foregoing embodiment, the accelerometer is a three-axis accelerometer.

A method of operating a radar presence detection system according to another, non-limiting, embodiment includes transmitting a monitoring wave by a transceiver of a radar; receiving a reflected wave by the transceiver; sending a reflected wave signal indicative of the reflected wave and by the radar to a processing unit; filtering a digitized reflected wave signal associated with the reflected wave signal by a filter of the processing unit to cancel a broadband of frequencies not within a targeted oscillation frequency range; outputting an oscillation reflected wave signal associated with the digitized reflected wave signal by the filter; detecting building vibrations by an accelerometer; sending a building vibration wave signal by the accelerometer to a second analog-to-digital converter of the processing unit; filtering a digitized vibration signal associated with the vibration wave signal by an adaptive filter of the processing unit to cancel a broadband of frequencies within the targeted oscillation frequency range; outputting a focused vibration signal associated with the digitized vibration signal by the adaptive filter; receiving the oscillation reflected wave signal and the focused vibration signal by a summation module; subtracting the focused vibration signal from the oscillation reflected wave signal; sending a corrected oscillation signal by the summation module to a detector; and evaluating the corrected oscillation signal by the detector to determine a presence.

Additionally to the foregoing embodiment, the processing unit is a vital sign processing unit, the targeted oscillation frequency range is a vital sign frequency range, the oscillation reflected wave signal is a vital sign reflected wave signal, the corrected oscillation signal is a corrected vital sign signal.

In the alternative or additionally thereto, in the foregoing embodiment, the presence is a human presence.

In the alternative or additionally thereto, in the foregoing embodiment, the method includes computing a transfer function by the adaptive filter associated with the location of the accelerometer relative to the radar.

In the alternative or additionally thereto, in the foregoing embodiment, the reflected wave signal is sent to a first analog-to-digital converter of the vital sign processing unit.

The foregoing features and elements may be combined in various combinations without exclusivity, unless expressly indicated otherwise. These features and elements as well as the operation thereof will become more apparent in light of the following description and the accompanying drawings. However, it should be understood that the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
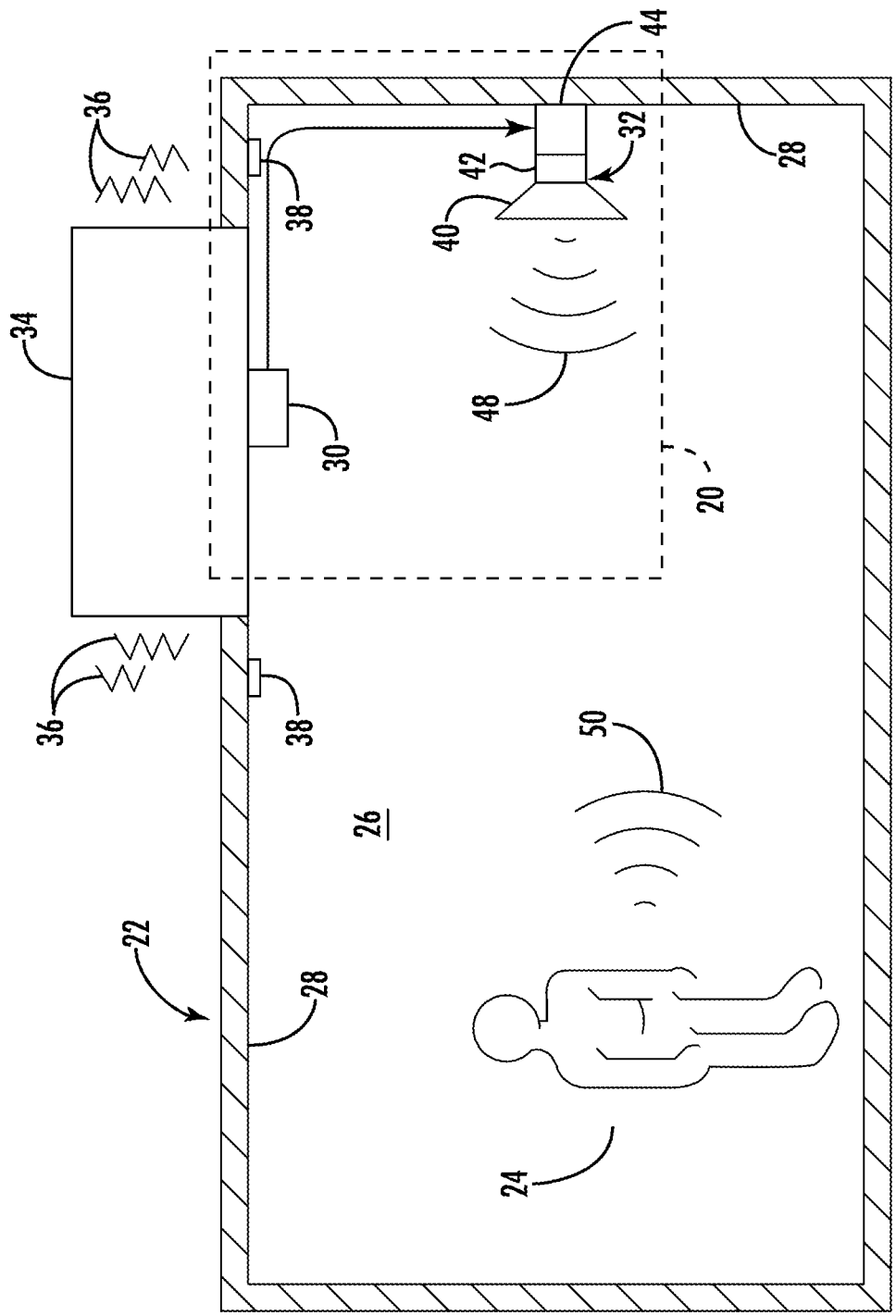
FIG. 1 is a schematic of a building incorporating a presence detection system as one, non-limiting, exemplary embodiment of the present disclosure.

Referring to FIG. 1, a radar detection system 20, which may be a radar presence detection system, is utilized in a building or structure 22 to detect the presence of a human 24 in a space 26 generally defined by an interior surface 28 of the building 22. The human detection is facilitated by the detection of oscillation that may be, for example, vital signs such as respiration and/or heartbeat. The radar presence detection system 20 may include an accelerometer 30, a radar 32, and a vital sign processing unit 44. The accelerometer 30 and the radar 32 may be mounted to the surface 28, but at different locations. In one example, the accelerometer 30 may be mounted proximate to building equipment 34 of the building 22 known to emit background vibrations 36. In another example, the accelerometer 30 may be a non-contacting method of measuring acceleration such as an additional radar or ultrasonic device. Other examples of background vibration 36 relevant to the present disclosure may include vibrations caused by weather conditions such as wind, outside traffic and/or trains, and other sources. Preferably, the accelerometer 30 is located between vibrational nodes 38 generally located upon the building surface 28. It is contemplated and understood that the vital sign processing unit may be an integral part of the radar electronics, and contained within a common housing of the radar 32.

It is contemplated and understood, that while the radar detection system 20 is generally taught as a detection system for the presence of a human through the detection of human vital signs, the present disclosure is also applicable to detecting the vital signs of animals and the vibrations or rotation of machinery.

Figure 2:
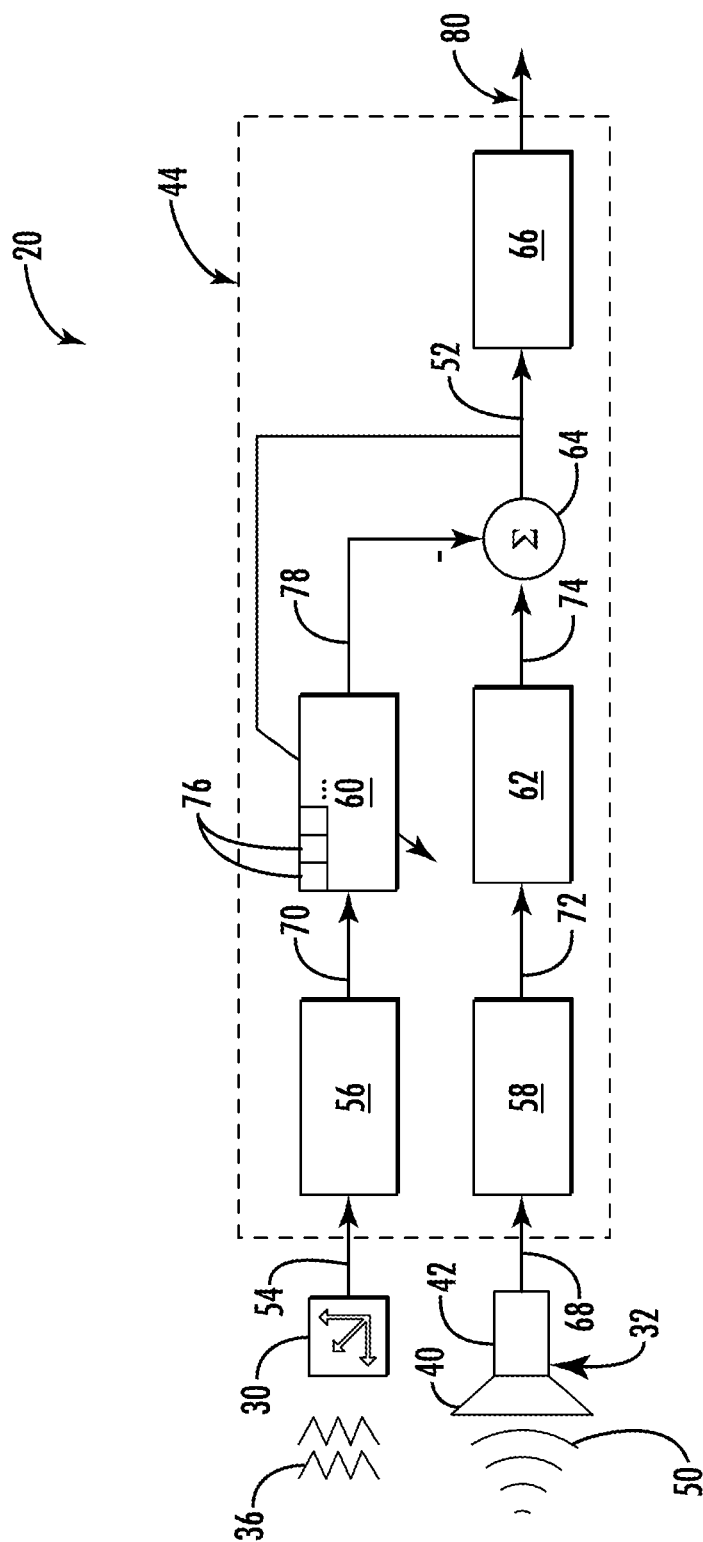
FIG. 2 is a schematic of the presence detection system.

Referring to FIGS. 1 and 2, the radar 32 of the presence detection system 20 may be configured to operate within a range of ten (10) GHz to about seventy-nine (79) GHz. The radar 32 may include an antenna 40, and a transceiver 42. In one example, monitoring waves or signals 48, which may be about 10 GHz microwaves, are transmitted by the transceiver 42 via the antenna 40. The transceiver 42 may comprise a transmitter and receiver that are entirely separate, or which may share hardware and software. The antenna 40 may comprise one or more physical antenna elements (i.e., phased array) that may be separate, for the transmitter and receiver respectively, or which may be combined for either or both the transmitter and receiver. The outgoing monitoring waves 48 may reflect off of the human 24 and return to the radar 32 as reflected waves 50 that are received by the transceiver 42 through the antenna 40, and generally processed and detected by the vital sign processing unit 44. The reflected waves 50 are indicative of a human respiration and/or a heartbeat, and may further include building background noise contributed by the building vibration 36 which may cause motion of either the human 24 or radar 32.

The antenna 40 generally emits and receives the waves 48, 50. The transceiver 42 is configured to transmit and receive the waves 48, 50 via the antenna 40, and amplifies, and/or frequency-converts, the received reflected waves 50. The vital sign processing unit 44 may detect the reflected waves 50 (e.g., microwaves) by amplitude, frequency, or phase detection, convert the waves from analog to digital, and filter out background noise from, for example, the building vibration 36, thereby producing corrected vital sign waves, or a corrected vital sign signal, 52 (see FIG. 2)

Referring to FIG. 2, the accelerometer 30 may be a three-axis accelerometer, hence outputting a three channel vibration wave signal 54 to the vital sign processing unit 44 for processing of each channel. The vital sign processing unit 44 may include a first analog-to digital converter (ADC) 56, a second ADC 58, an adaptive filter 60 (i.e., LMS), a low pass filter 62, a summation module 64 and a detector 66. In operation, the building vibrations 36 are detected by the accelerometer 30 and outputted as the vibration wave signal 54 to the ADC 56 for conversion from analog to digital. The vibration wave signal 54 may be amplified by the accelerometer 30 prior to sending to the ADC 56. The reflected waves 50 are received by the transceiver 42 of the radar 32 via the antenna 40, may be amplified, and then sent to the ADC 58 as a reflected wave signal 68 for conversion from analog to digital.

The ADC 56 is configured to send a digitized vibration signal 70 to the adaptive filter 60. Similarly, the ADC 58 is configured to send a digitized reflected wave signal 72 to the filter 62. In operation, the filter 62 filters the signal 72 to a range of human vital signs. For example, a normal heart rate may be 60 to 180 beats per minute equating to about one (1) to three (3) Hz, and a typical respiratory rate is about ten (10) to twenty (20) breadths per minute equating to about 0.15 to 0.3 Hz. Accordingly, any other harmonics and out-of-band noise, other than that associated with the vital sign frequency range(s), can be filtered out by employing the filter 62. When filtered, the incoming digitized reflected wave signal 72 is processed into an outgoing vital sign reflected wave signal 74.

The adaptive filter 60 may be a long adaptive filter having sufficient taps 76 so that a full wave at the lowest respiration frequency (i.e., 0.15 Hz) may be accommodated. More specifically, the adaptive filter 60 facilitates the cancellation of broadband vibration, and not a specific number or range of harmonics. Therefore, the adaptive filter 60 includes a multitude of taps 76, wherein the number of taps 76 is not related to a number of harmonics. It is noted that the adaption rate of the filter 60 may be slow since the adaptive filter 60 may be computing a transfer function of the building 22 associated with the location of the accelerometer 30 relative to the radar 32. In one embodiment, the transfer function may be estimated once at the installation of the presence detection system 20 and used thereafter. However, in another embodiment, the transfer function is updated during operation. One, non-limiting, example of the adaptive filter 60 may be a least-mean-square (LMS) filter. Other filter 60 examples may include Normalized Least-Mean-Square (NLMS), Recursive Least Squares (RLS), and Sample or Direct Matrix Inversion (DMI) filters.

The adaptive filter 60 is configured to filter the vibration signal 70 to enable cancelling a broadband of vibration frequencies within the frequency range of human vital signs by outputting a focused vibration signal 78 associated with noise within the human vital sign frequency range(s). The summation module 64 is configured to receive the signals 74, 78, subtract the focused vibration signal 78 from the vital sign reflected wave signal 74, and output the corrected, or noise reduced, vital sign signal 52 to the detector 66. The focused vibration signal 78 may be produced as the output of a Finite Impulse Response (FIR) filter with adapted coefficients based on the vibration signal 70 and the corrected vital signal 52 using a LMS update. The FIR filter is effectively the transfer function from the vibration signal 70 to the vital sign reflected wave signal 74. The detector 66 is configured to evaluate the corrected vital sign signal 52, determine the presence of a human, and output an oscillation or presence signal 80 that may be indicative of the presence and/or non-presence of the human 24.

The presence signal 80 may be used by any number of systems commonly applied in a building 22. For example, the signal 80 may be used by a security system attempting to detect intrusions, by a heating and/or cooling system attempting to save energy when, for example, a building is vacant, and/or a safety or fire protection system attempting to locate people during a fire scenario. Other systems including building management systems may be further enhanced via the use of the presence detection system 20.

Figure 3:
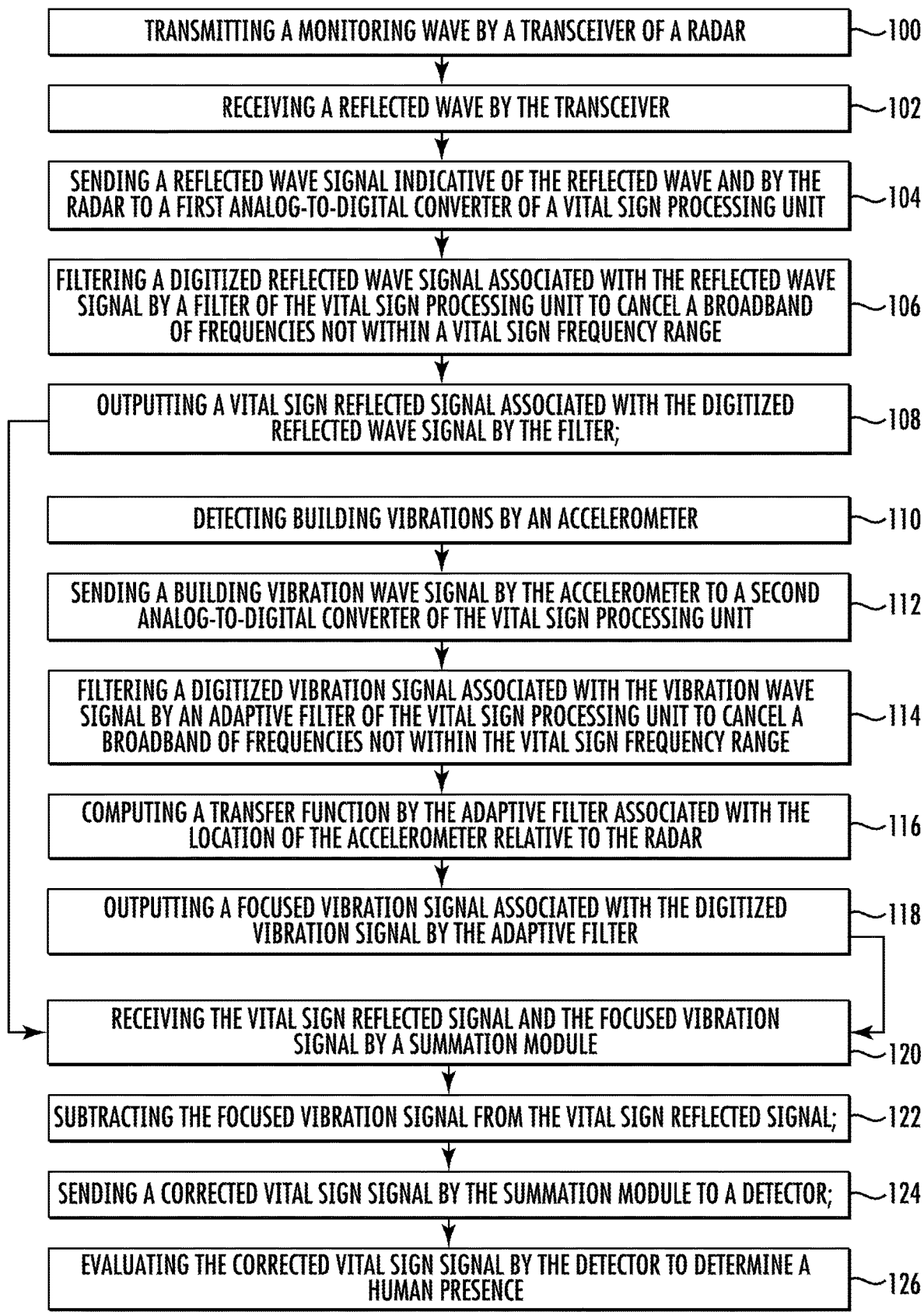
FIG. 3 is a flow chart of a method of operating the presence detection system.

Referring to FIG. 3, a method of operating the presence detection system 20 is illustrated. At block 100, a monitoring wave 48 is transmitted by a transceiver 42 of radar 32. At block 102, a reflected wave 50 is received by the transceiver 42. At block 104, a reflected wave signal 68, indicative of the reflected wave 50, is sent by the radar 32 to a first analog-to-digital converter 58 of a vital sign processing unit 44. At block 106, a digitized reflected wave signal 72, associated with the reflected wave signal 68, is filtered by a filter 62 of the vital sign processing unit 44 to cancel a broadband of frequencies not within a targeted oscillation frequency range (e.g., vital sign frequency range). At block 108, an oscillation reflected wave signal 74 (e.g., vital sign reflected wave signal) associated with the digitized reflected wave signal 72 is outputted by the filter 62.

The detection and processing of building vibrations may occur simultaneously to the events of blocks 100 through 108. More specifically and at block 110, building vibrations are detected by an accelerometer 30. At block 112, a vibration wave signal 54 associated with the building vibration is sent by the accelerometer to a second ADC 56 of the vital sign processing unit 44. At block 114, a digitized vibration signal 70 associated with the vibration wave signal 54 is filtered by an adaptive filter 60 of the vital sign processing unit 44 to enable cancelation of a broadband of frequencies within the vital sign frequency range. At block 116, a transfer function associated with the location of the accelerometer 30 relative to the radar 32 is updated by the adaptive filter 60. At block 118, a focused vibration signal 78 associated with the digitized vibration signal 70 is outputted by the adaptive filter 60.

At block 120, the vital sign reflected wave signal 74 and the focused vibration signal 78 are received by a summation module 64. At block 122, the summation module 64 subtracts the focused vibration signal 78 from the vital sign reflected wave signal 74. At block 124, a corrected oscillation signal 52 (e.g., corrected vital sign signal) is sent by the summation module 64 to the detector 66 and to adaptive filter 60. At block 126, the corrected vital sign signal is evaluated by the detector 66 to determine a human presence.

Figure 4:
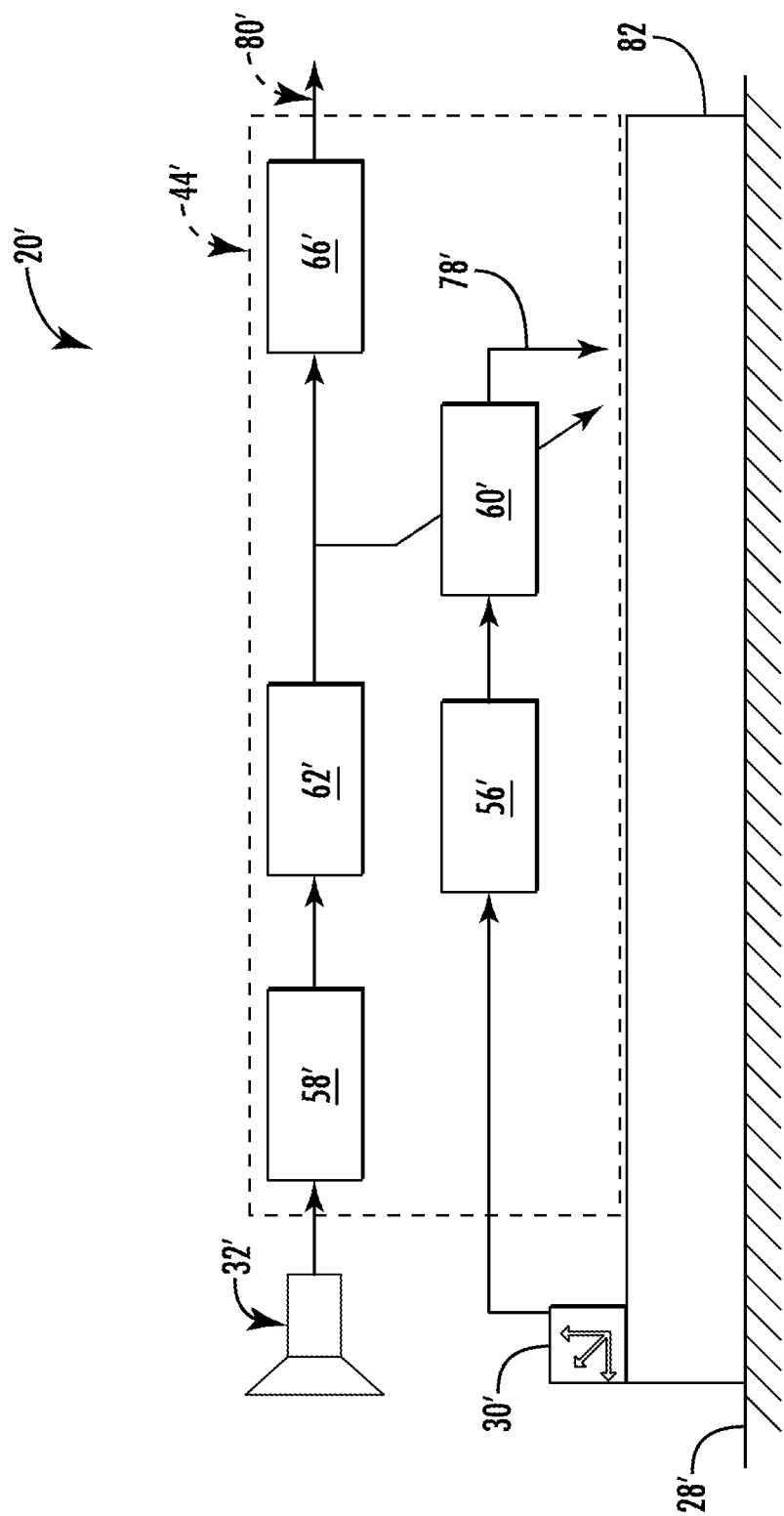
FIG. 4 is a schematic of a second embodiment of a presence detection system.

Referring to FIG. 4, a second embodiment of a presence detection system is illustrated wherein like elements to the first embodiment have like identifying numbers except with the addition of a prime symbol suffix. A presence detection system 20' includes an accelerometer 30', a radar 32', a vital sign processing unit 44', and an actuator 82 mounted to a surface 28'. The accelerometer 30' may be attached to the actuator 82. In one embodiment, the accelerometer 30', the radar 32', the vital sign processing unit 44', and the actuator 82 may be contained in a common housing and co-located. The actuator 82 is constructed and arranged to physically move the radar 32' in order to cancel out any noise produced by building vibration.

The vital sign processing unit 44' may include a first analog-to digital converter (ADC) 56', a second ADC 58', an adaptive filter 60' (i.e., LMS), a low pass filter 62', and a detector 66'. The adaptive filter 60' outputs a focused vibration signal 78' to the actuator 82. The adaptive filter 60' is configured to drive the actuator 82 in an opposite motion to the sensed motion (i.e., vibration) of the surface 28', thereby effectively isolating the radar 32' from building vibration.

Advantages and benefits of the present disclosure include an efficient, effective, and/or accurate radar human vital sign detection in the presence of complex vibration of the radar sensor from the mounting structure.

While the present disclosure is described with reference to exemplary embodiments, it will be understood by those skilled in the art that various changes may be made and equivalents may be substituted without departing from the scope of the present disclosure. In addition, various modifications may be applied to adapt the teachings of the present disclosure to particular situations, applications, and/or materials, without departing from the essential scope thereof. The present disclosure is thus not limited to the particular examples disclosed herein, but includes all embodiments falling within the scope of the appended claims.

What is claimed is:

1. A radar presence detection system configured to detect oscillations within a building, the radar detection system comprising:
    an accelerometer attached to the building and configured to detect structural vibration waves;

a radar configured to transmit a monitoring wave and receive a reflected wave; and a processing unit configured to receive a reflected wave signal from the radar indicative of the reflected wave, and a vibration wave signal indicative of the structural vibration wave, the processing unit including a filter, an adaptive filter and a detector, wherein the filter is configured to receive a first signal indicative of the reflected wave signal and output a filtered reflected wave signal spanning a frequency range indicative of an oscillation within the building, and the adaptive filter being configured to receive a second signal indicative of the structural vibration wave signal and output a focused vibration signal spanning the frequency range for the cancellation of vibration noise, and wherein the detector is configured to receive a third signal indicative of at least the filtered reflected wave signal and output an oscillation signal indicative of at least the detection of the oscillation;

wherein the processing unit is a vital sign processing unit, the filtered reflected wave signal is a vital sign reflected wave signal, and the oscillation is a vital sign;

wherein the vital sign processing unit includes a first analog-to-digital converter configured to receive the reflected wave signal and output a digitized reflected wave signal as the first signal;

wherein the vital sign processing unit includes a second analog-to-digital converter configured to receive the vibration wave signal and output a digitized vibration signal as the second signal, and wherein the adaptive filter is configured to cancel a broad band of vibration frequencies within the frequency range; and wherein the vital sign processing unit includes a summation module configured to receive the vital sign reflected wave signal and the focused vibration signal, subtract the focused vibration signal from the vital sign reflected wave signal, and output a corrected vital sign signal received by the detector.

2. The radar presence detection system set forth in claim 1, wherein the adaptive filter is a long adaptive filter.

3. The radar presence detection system set forth in claim 1, wherein the filtered reflected wave signal is a vital sign reflected wave signal, and wherein the vital sign processing unit includes a summation module configured to receive the vital sign reflected wave signal and the focused vibration signal, subtract the focused vibration signal from the vital sign reflected wave signal, and output a corrected vital sign signal received by the detector.

4. The radar presence detection system set forth in claim 1, wherein the adaptive filter includes a plurality of taps with a sufficient number of taps so that a full wave at a minimum respiration frequency is accommodated.

5. The radar presence detection system set forth in claim 1, wherein the oscillation is at least one vital sign that includes at least one of a respiration rate and a heartbeat.

6. The radar presence detection system set forth in claim 1, wherein the radar is remotely located from the accelerometer.

7. The radar presence detection system set forth in claim 1 further comprising:

an actuator attached to the building and the accelerometer, wherein the actuator receives and is driven by the focused vibration signal to cancel vibration noise.

8. The radar presence detection system set forth in claim 1, wherein the adaptive filter is at least one of a LMS filter, a NLMS filter, a RLS filter, and a DMI filter.

9. The radar presence detection system set forth in claim 1, wherein the accelerometer is not located at any vibration node of the building.

10. The radar presence detection system set forth in claim 7, wherein the accelerometer is co-located with the radar.

11. The radar presence detection system set forth in claim 1, wherein the accelerometer is a three-axis accelerometer.

12. A method of operating a radar presence detection system comprising:

transmitting a monitoring wave by a transceiver of a radar;

receiving a reflected wave by the transceiver;

sending a reflected wave signal indicative of the reflected wave and by the radar to a processing unit;

filtering a digitized reflected wave signal associated with the reflected wave signal by a filter of the processing unit to cancel a broadband of frequencies not within a targeted oscillation frequency range;

outputting an oscillation reflected wave signal associated with the digitized reflected wave signal by the filter;

detecting building vibrations by an accelerometer;

sending a building vibration wave signal by the accelerometer to a second analog-to-digital converter of the processing unit;

filtering a digitized vibration signal associated with the vibration wave signal by an adaptive filter of the processing unit to cancel a broadband of frequencies within the targeted oscillation frequency range;

outputting a focused vibration signal associated with the digitized vibration signal by the adaptive filter;

receiving the oscillation reflected wave signal and the focused vibration signal by a summation module;

subtracting the focused vibration signal from the oscillation reflected wave signal;

sending a corrected oscillation signal by the summation module to a detector; and evaluating the corrected oscillation signal by the detector to determine a presence.

13. The method set forth in claim 12, wherein the processing unit is a vital sign processing unit, the targeted oscillation frequency range is a vital sign frequency range, the oscillation reflected wave signal is a vital sign reflected wave signal, the corrected oscillation signal is a corrected vital sign signal.

14. The method set forth in claim 13, wherein the presence is a human presence.

15. The method set forth in claim 12 further comprising:

computing a transfer function by the adaptive filter associated with the location of the accelerometer relative to the radar.

16. The method set forth in claim 12, wherein the reflected wave signal is sent to a first analog-to-digital converter of the vital sign processing unit.

* * * * *